(12) United States Patent
Hannen et al.

(10) Patent No.: US 8,431,742 B2
(45) Date of Patent: Apr. 30, 2013

(54) METHOD FOR PRODUCING DODECA-2,10-DIENE-1,12-DICARBOXYLIC ACID OR 1,12-DODECANE-DICARBOXYLIC ACID BY WAY OF RING-OPENING CROSS METATHESIS (ROCM) OF CYCLOOCTENE WITH ACRYLIC ACID

(75) Inventors: Peter Hannen, Recklinghausen (DE); Martin Roos, Haltern am See (DE); Harald Haeger, Luedinghausen (DE)

(73) Assignee: Evonik Degussa GmbH, Essen (DE)

( * ) Notice: Subject to any disclaimer, the term of this patent is extended or adjusted under 35 U.S.C. 154(b) by 330 days.

(21) Appl. No.: 12/922,807

(22) PCT Filed: Apr. 16, 2009

(86) PCT No.: PCT/EP2009/054519
§ 371 (c)(1),
(2), (4) Date: Sep. 15, 2010

(87) PCT Pub. No.: WO2009/144089
PCT Pub. Date: Dec. 3, 2009

(65) Prior Publication Data
US 2011/0015434 A1    Jan. 20, 2011

(30) Foreign Application Priority Data

May 30, 2008 (DE) .......................... 10 2008 002 092

(51) Int. Cl.
*C07C 51/353* (2006.01)
*C07C 51/43* (2006.01)
*C07C 51/44* (2006.01)
*C07C 57/13* (2006.01)

(52) U.S. Cl.
USPC ....................................................... 562/595

(58) Field of Classification Search ........................ None
See application file for complete search history.

(56) References Cited

U.S. PATENT DOCUMENTS

| | | |
|---|---|---|
| 6,828,449 B2 | 12/2004 | Herwig et al. |
| 6,861,540 B2 | 3/2005 | Herwig et al. |
| 6,927,308 B2 | 8/2005 | Leininger et al. |
| 7,084,300 B2 | 8/2006 | Herwig et al. |
| 7,253,329 B2 | 8/2007 | Herwig et al. |
| 7,495,129 B2 | 2/2009 | Balduf et al. |
| 7,608,738 B2 | 10/2009 | Herwig et al. |
| 2007/0004903 A1 | 1/2007 | Hoff et al. |
| 2007/0265184 A1 | 11/2007 | Herwig et al. |
| 2009/0306367 A1 | 12/2009 | Roos et al. |

OTHER PUBLICATIONS

Saito, Isao et al., "Synthesis of Synthetic alpha, omega-Dicarboxylic Acids and Unsaturated Carboxylic Acids from Silyl Enol Ethers", Tetrahedron Letters, vol. 24, No. 41, pp. 4439-4442, XP002529873, (1983).
Randl, Stefan et al., "Ring opening-cross metathesis of unstrained cycloalkenes", Chemical Communications, Chemcomm Communication, Journal the Royal Society of Chemistry, pp. 1796-1797, XP002334391, ISSN: 1359-7345, (Nov. 4, 2001).
U.S. Appl. No. 12/865,018, filed Jul. 28, 2010, Hannen et al.
U.S. Appl. No. 13/424,548, filed Mar. 20, 2012, Hannen et al.
U.S. Appl. No. 13/142,505, filed Jun. 28, 2011, Meier et al.
U.S. Appl. No. 13/634,111, filed Sep. 11, 2012, Petrat et al.

*Primary Examiner* — Yevegeny Valenrod
(74) *Attorney, Agent, or Firm* — Oblon, Spivak, McClelland, Maier & Neustadt, L.L.P.

(57) ABSTRACT

The invention relates to a method for producing 1,2-dodeca-2,10-diene diacid and 1,12-dodecanoic acid whereby cyclooctene and acrylic acid are reacted with a ruthenium catalyst by way of a metathesis reaction at high substrate concentrations until the reaction takes place in substance, the resulting unsaturated dicarboxylic acid being precipitated and being hydrated in a second reaction step.

20 Claims, No Drawings

METHOD FOR PRODUCING DODECA-2,10-DIENE-1,12-DICARBOXYLIC ACID OR 1,12-DODECANE-DICARBOXYLIC ACID BY WAY OF RING-OPENING CROSS METATHESIS (ROCM) OF CYCLOOCTENE WITH ACRYLIC ACID

Alkyldicarboxylic acids are important compounds for the preparation of plastics such as polyesters and polyamides. Particular mention may be made of high-performance plastics based on polyamides, as are used, for example, for the production of fuel lines. One of these dicarboxylic acids is 1,12-dodecanedicarboxylic acid (DDA). As industrial processors for preparing DDA, particular mention may be made of:

cleavage of cyclododecanol by means of concentrated nitric acid; Invista and Degussa oxidative coupling and opening of cyclohexanone by means of $H_2O_2$; Ube biotechnological processes in which n-dodecane is terminally oxidized to form DDA; Cathay Biotechnology and others.

These processes are energy-intensive and produce large quantities of waste which is expensive to dispose of. In addition, the selectivity is often not high. Thus, for example, in the oxidative cleavage of cyclododecanol by means of nitric acid, the formation of short-chain "breakup acids" by oxidative degradation is a problem.

A new approach to the preparation of dicarboxylic acids is metathesis. A combination of ring-opening metatheses (ROM) with cross metathesis (CM) makes it possible to prepare aliphatic $\alpha,\beta$-unsaturated dicarboxylic acids in one step from cycloalkenes and acrylic acid using suitable precatalysts. If cyclooctene (1) as starting material is reacted with acrylic acid (2), dodecane-2,10-diene-1,12-dicarboxylic acid (3) is obtained (scheme 1). The combination of the two reaction steps is also referred to as ROCM (ring-opening cross metathesis) or ROX metathesis.

Scheme 1: Reaction of COE with acrylic acid to form compound 3.

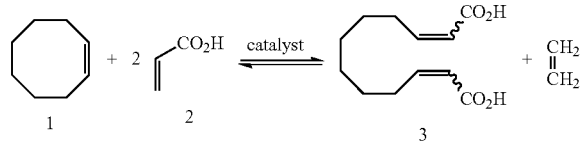

The $\alpha,\beta$-unsaturated dicarboxylic acid obtained can be hydrogenated in a second step to give the desired 1,12-dodecanedicarboxylic acid (4) (scheme 2).

Scheme 2: Hydrogenation of dodeca-2,10-diene-1,12-dicarboxylic acid to DDA.

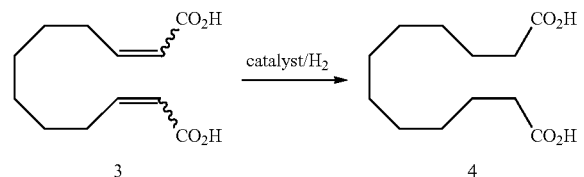

Moreover, it is also conceivable to use the unsaturated dicarboxylic acid as monomer for the preparation of unsaturated polyamides or polyesters. The polymers obtained in this way can subsequently be crosslinked, which is of interest for many applications.

Metathesis reactions are equilibrium reactions giving a corresponding product distribution. The above-described reaction can take various reaction paths. Thus, the cycloalkene can react in a ring-opening metathesis polymerization to form a polyolefin. Furthermore, formation of various telechelic oligomers can occur. These secondary reactions have an adverse effect on the yield of desired product and also make work-up of the reaction mixture difficult. The formation of ethylene, which can be taken off as gas from the liquid phase, results in a shift of the equilibrium in the direction of the product. However, this effect is not sufficient to suppress secondary reactions such as polymerization completely.

PRIOR ART

In the prior art to date, (Morgan, John, P., Morrill, Christie; Grubbs, Robert, H.; Choi, Tae-Lim WO 02/079127 A1, Choi, T-L.; Lee, C. W.; Chatterjee, A. K.; Grubbs, R. H. J. Am. Chem. Soc. 2001, 123, 10417-10418, Randl, S.; Connon, S. J.; Blechert, S. J. Chem. Soc., Chem. Commun. 2001, 1796-1797), the reaction is carried out in dilute solutions (c~0.2 M) in order to push the reaction in the direction of the low molecular weight products. Column chromatography using silica gel is predominantly employed for working up the reaction mixture and separating off the catalyst. Furthermore, dichloromethane, which is considered to be problematical for an industrial reaction, is predominantly used as solvent. Working at a high dilution, the consumption of large amounts of solvents in the work-up and the use of solvents which are hazardous to health stand in the way of the concept of a durable process which is to form the basis of industrial implementation.

It has now surprisingly been found that a process according to the claims makes it possible to shift the equilibrium completely in the direction of the desired product without working at a high dilution. In addition, the process described makes effective recycling of the catalyst possible. This is achieved by, in contrast to previous practice, working at high substrate concentrations up to reactions in bulk. During the course of the reaction, the $\alpha,\beta$-unsaturated dicarboxylic acid precipitates when the solubility product is exceeded and is thus removed from the equilibrium (in the homogeneous phase). This adds a second positive effect to the shifting of the equilibrium in the direction of the desired product by formation of gaseous ethylene.

A further challenge is separating off and, if appropriate, recycling the catalyst. The catalyst often has to be separated off by column chromatography in a complicated operation, which makes industrial implementation uneconomical.

As a result of the product being obtained as a solid in the process described here, this can easily be filtered off, purified and the catalyst dissolved in the filtrate can be recycled.

The reaction described is carried out at temperatures of from 10 to 100° C., preferably from 20 to 80° C. and particularly preferably from 20 to 60° C.

The reaction described can be carried out in bulk or using a solvent. Suitable solvents are acyclic and also cyclic hydrocarbons. Aromatic halogenated hydrocarbons are particularly suitable and aromatics having alkyl groups are very particularly suitable.

When the reaction is carried out in solution, cyclooctene concentrations of >1 M are preferred. Particular preference is given to cyclooctene concentrations of from 1 to 2 M and very particular preference is given to cyclooctene concentrations of from 2 to 4 M, based on the solvent.

In the process described, the catalyst is used in amounts of from 5 to 0.0001 mol %, based on the amount of cyclooctene. Preference is given to amounts of from 2 to 0.001 mol % and particular preference is given to amounts of from 1 to 0.5 mol % of catalyst, based on the molar amount of cyclooctene used.

To obtain the α,β-unsaturated dicarboxylic acid in polymer grade quality, purification by crystallization, distillation or a combination of the two is possible.

Suitable catalysts are ruthenium-carbene complexes which, as one of the characteristic features, bear an N-heterocyclic carbene ligand. Examples of preferred catalysts are shown in FIG. 1. Particular preference is given to catalysts of the type 7, with an electron-withdrawing group R' on the benzylidene ligand.

FIG. 1: Examples of ruthenium catalysts used.

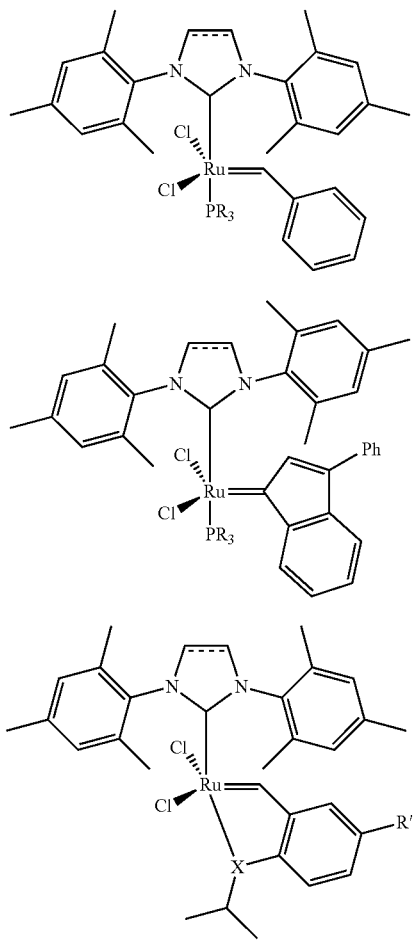

EXAMPLES 1. 1,3-Bis(2,4,6-trimethylphenyl)-4,5-dihydroimidazol-2-ylidene[2-(i-propoxy)-5-(N,N-dimethylaminosulphonyl) phenyl]methyleneruthenium(II) dichloride (0.333 g, 0.45 mmol) is placed together with acrylic acid (13.09 g, 0.182 mol) under argon in a three-necked flask provided with reflux condenser and the mixture is heated to 60° C. Cyclooctene (10 g, 0.091 mol) is added dropwise over a period of 20 minutes. After 1.5 hours, the reaction mixture is allowed to cool to room temperature and is admixed with toluene (200 ml). It is briefly heated to boiling and subsequently cooled slowly while stirring. The solid which has precipitated is filtered off and washed with cold toluene (3×10 ml). After drying under reduced pressure, the product is obtained as a white solid (10.2 g, 50%). According to NMR analysis, the product has a purity of >99%.

2. A mixture of cyclooctene (10 g, 0.091 mol) and acrylic acid (13.09 g, 0.182 mol) in toluene (20 ml) was heated to 60° C. 10 ml of a solution of 1,3-bis(2,4,6-trimethylphenyl)-4,5-dihydroimidazol-2-ylidene[2-(i-propoxy)-5-(N,N-dimethylaminosulphonyl)phenyl]methyleneruthenium(II) dichloride (0.667 g, 0.00091 mol) in toluene (25 ml) are firstly added and the remaining 15 ml are added dropwise over a period of one hour. After the addition is complete, the mixture is stirred at the indicated temperature for one hour and is then cooled. The precipitated solid is filtered off and washed with cold toluene (3×5 ml). After drying under reduced pressure, the product is obtained as a white solid (10.2 g, 50%). According to NMR analysis, the product has a purity of >99%.

The invention claimed is:

1. A process for preparing dodeca-2,10-diene-1,12-dioic acid of the formula,

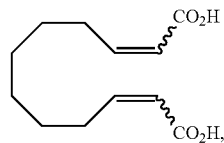

comprising reacting cyclooctene and acrylic acid by a metathesis reaction in the presence of a ruthenium catalyst, optionally, in bulk, and thereby precipitating the dicarboxylic acid formed from a reaction mixture.

2. The process according to claim 1, further comprising hydrogenating the unsaturated dodeca-2,10-diene-1,12-dioic acid obtained to dodecane-1,12-dioic acid after the reacting.

3. The process according to claim 1, wherein cyclooctene is present in a concentration of >1 mol/L when the reacting is carried out in solution.

4. The process according to claim 1, wherein cyclooctene is present in a concentration of from 2 to 4 mol/L when the reacting is carried out in solution.

5. The process according to claim 1, wherein at least one ruthenium-carbene complex comprising an N-heterocyclic ligand is employed as a catalyst.

6. The process according to claim 1, wherein the ruthenium catalyst is employed in an amount of from 5 to 0.0001 mol % based on a molar amount of cyclooctene.

7. The process according to claim 1, wherein the ruthenium catalyst is employed in an amount of from 2 to 0.001 mol % based on a molar amount of cyclooctene.

8. The process according to claim 1, wherein the ruthenium catalyst is employed in an amount of from 1 to 0.5 mol % based on a molar amount of cyclooctene.

9. The process according to claim 1, wherein at least one acyclic or cyclic hydrocarbon is employed as solvents.

10. The process according to claim 1, wherein at least one aromatic halogenated hydrocarbon is employed as a solvent.

11. The process according to claim 1, further comprising recycling the ruthenium catalyst dissolved in a filtrate after a separating the precipitate from the reaction mixture.

12. The process according to claim 1, further comprising purifying unsaturated dicarboxylic acid obtained by at least one selected from the group consisting of crystallization and distillation.

13. The process according to claim 2, wherein at least one ruthenium-carbene complex comprising an N-heterocyclic ligand is employed as a catalyst.

14. The process according to claim 3, wherein at least one ruthenium-carbene complex comprising an N-heterocyclic ligand is employed as a catalyst.

15. The process according to claim 4, wherein at least one ruthenium-carbene complex comprising an N-heterocyclic ligand is employed as a catalyst.

16. The process according to claim 2, wherein the ruthenium catalyst is employed in an amount of from 5 to 0.0001 mol % based on a molar amount of cyclooctene.

17. The process according to claim 3, wherein the ruthenium catalyst is employed in an amount of from 5 to 0.0001 mol % based on a molar amount of cyclooctene.

18. The process according to claim 4, wherein the ruthenium catalyst is employed in an amount of from 5 to 0.0001 mol % based on a molar amount of cyclooctene.

19. The process according to claim 5, wherein the ruthenium catalyst is employed in an amount of from 5 to 0.0001 mol % based on a molar amount of cyclooctene.

20. The process according to claim 13, wherein the ruthenium catalyst is employed in an amount of from 5 to 0.0001 mol % based on a molar amount of cyclooctene.

\* \* \* \* \*